United States Patent [19]
Stendahl et al.

[11] Patent Number: 6,083,246
[45] Date of Patent: Jul. 4, 2000

[54] LID OPEN DETECTION CIRCUIT FOR AUTOMATED EXTERNAL DEFIBRILLATORS

[75] Inventors: Gary B. Stendahl, Crystal; Michael D. Welsch, Woodbury, both of Minn.

[73] Assignee: SurVivaLink Corporation, Minneapolis, Minn.

[21] Appl. No.: 09/057,031

[22] Filed: Apr. 8, 1998

Related U.S. Application Data

[60] Provisional application No. 60/042,756, Apr. 8, 1997.

[51] Int. Cl.⁷ ..................................................... A61N 1/39
[52] U.S. Cl. .................................................................. 607/5
[58] Field of Search ............................................. 607/4, 5

[56] References Cited

U.S. PATENT DOCUMENTS

| | | |
|---|---|---|
| 5,237,989 | 8/1993 | Morgan et al. . |
| 5,579,234 | 11/1996 | Wiley et al. . |
| 5,607,454 | 3/1997 | Cameron et al. ............................. 607/5 |
| 5,697,955 | 12/1997 | Stolte ........................................... 607/5 |

OTHER PUBLICATIONS

*SurVivaLink AED Automatic External Defibrillator System*, SurVivaLink Brochure, SurVivaLink Corporation, 4 pages, Nov. 1993.

*Primary Examiner*—Kennedy J. Schaetzle
*Attorney, Agent, or Firm*—Patterson & Keough, P.A.

[57] ABSTRACT

A lid open detection circuit for powering ON an automated external defibrillator having a housing and an openable lid formed in the housing, generally incorporates a switch that has a first state for powering ON the AED when the openable lid is open and a second state for powering OFF the AED when the openable lid is closed. The switch is preferably a Hall effect switch.

6 Claims, 6 Drawing Sheets

LID OPEN DETECTION CIRCUIT FOR AUTOMATED EXTERNAL DEFIBRILLATORS

RELATED APPLICATION

This application claims the benefit of U.S. Provisional Application No. 60/042,756, filed Apr. 8, 1997.

TECHNICAL FIELD

The present invention relates generally to automated external defibrillators. In particular, the present invention is a lid open detection circuit for an automated external defibrillator wherein the lid open detection circuit powers ON the automated external defibrillator thereby initiating the automatic operation of the automated external defibrillator.

BACKGROUND OF THE INVENTION

Cardiac arrest, or heart fibrillation, is the rapid and uncoordinated contraction of the cardiac muscle. The use of external defibrillators to restore the heartbeat to its normal pace through the application of an electrical shock is a well recognized and important tool for resuscitating patients. External defibrillation is typically used in emergency settings in which the patient is either unconscious or otherwise unable to communicate.

Automated external defibrillators or AEDs are used by police officers, paramedics and other first-responder emergency medical technicians to resuscitate patients in fibrillation. It is important that the AEDs carried by these technicians be continuously operational and ready for use on a moments notice. It is essential that in a high stress situation of cardiac arrest, the technician be able to focus on the patient and not on what buttons need be depressed to turn on the AED. Studies have shown that the chances of successfully resuscitating a patient decreases approximately ten percent per minute following fibrillation, thus the consequences of having to fumble with a "power on" switch that may be confusingly placed among a multitude of switches can have severe consequences. There is, therefore, a need for a lid open detection circuit that is capable of reliably powering on an AED without the need for actual depression of a "power on" button.

SUMMARY OF THE INVENTION

The problems outlined above are in large measure solved by a lid open detection circuit for automated external defibrillators in accordance with the present invention. The lid open detection circuit hereof for powering ON an automated external defibrillator having a housing and an openable lid formed in the housing, generally incorporates a switch that has a first state for powering ON the AED when the openable lid is open and a second state for powering OFF the AED when the openable lid is closed. The switch is preferably a Hall effect switch.

DETAILED DESCRIPTION

Referring to FIG.'S 1–5, a lid open detection circuit 8 for automated external defibrillators (AEDs) 10 in accordance with the present invention may be appreciated. The lid open detection circuit 8 is adapted to power ON AED 10 thereby initiating the automatic operation of AED 10.

Figure 1:
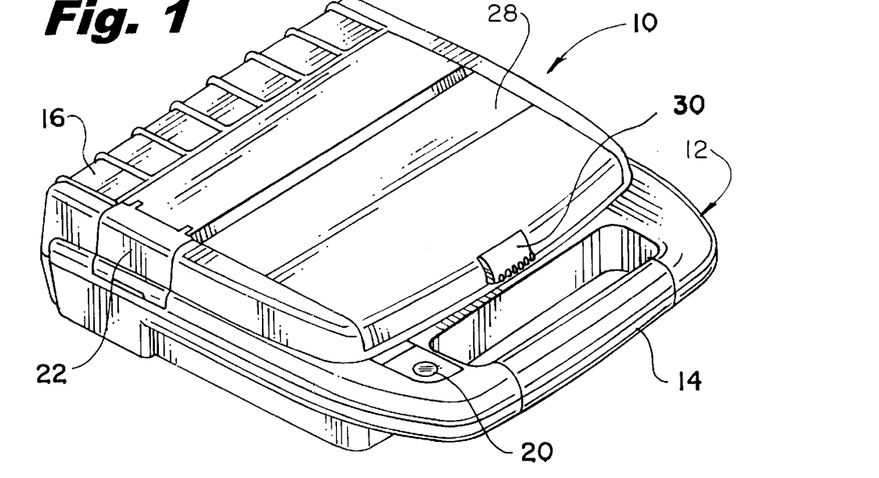
FIG. 1 is a perspective view of an automated external defibrillator (AED).

As shown AED 10 includes a plastic case 12 with a carrying handle 14 on the front portion. A battery compartment (not visible) in the rear portion of AED 10 encloses a battery pack 16, the battery pack being removably disposed within the battery compartment. A visual maintenance indicator 20 and a data access door 22, which conceals a serial connector port 23 and a data card slot 24, are located on the outside of case 12 for easy access by an operator.

Case 12 also includes an electrode compartment 26 defined in the top portion of case 12. A resume/rescue switch 18 (depicted in FIG. 2) is disposed adjacent to electrode compartment 26. Electrode compartment 26 is enclosed by lid 28 which is mounted to case 12 by hinges (not visible). Lid 28 covers resume/rescue switch 18 when lid 28 is in the closed position, as depicted in FIG. 1. Resume/rescue switch 18 is actually a single switch with illuminatable labels alternatively indicating the "resume" or the "rescue" function, "rescue" appearing above switch 18 and "resume" appearing below switch 18, depending on whether AED 10 is cuing the operator to perform a rescue or resume operation by activating switch 18. A magnet 29 is incorporated into the underside of lid 28.

Figure 2:
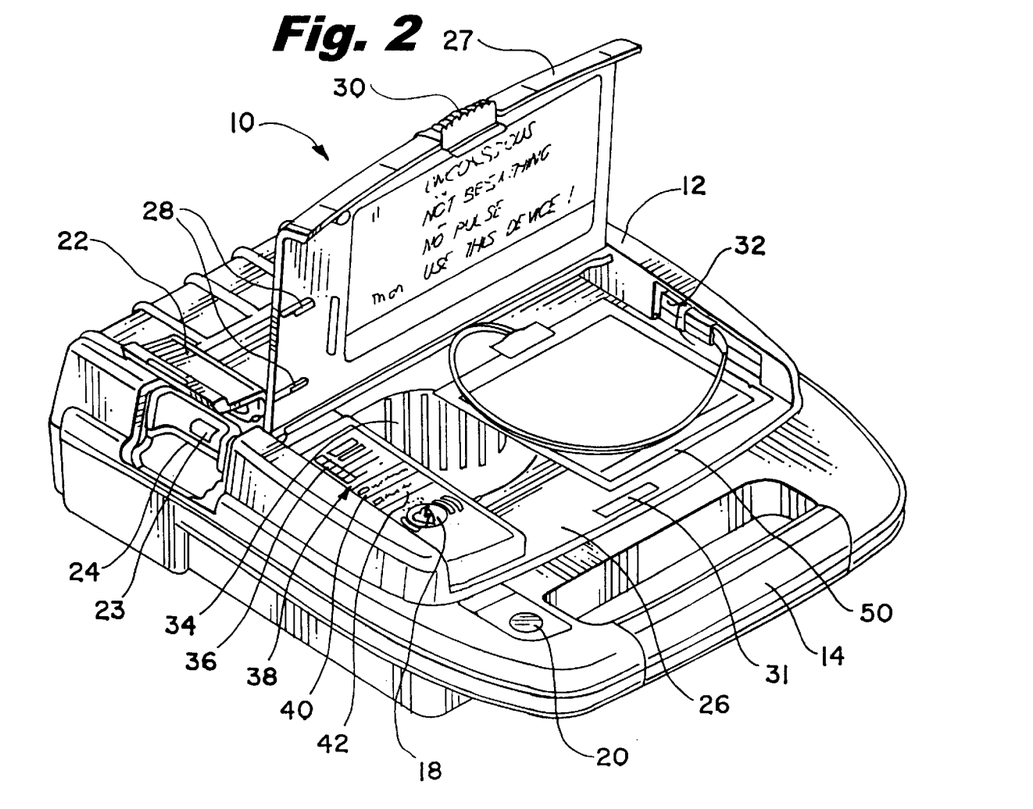
FIG. 2 is a perspective view of the AED with its lid open.

The inside of lid 28 incorporates a data card storage clasp 29 for holding a data card (not shown). A bayonet-type releasable latch 30 holds lid 28 closed when AED 10 is not in use by engaging a receiving recess 31 defined in the floor of electrode compartment 26. Lid 28 is opened by grasping the underside of latch 30, pushing in to disengage latch 30 from recess 31 and lifting upward on latch 30 to gain access to electrode compartment 26.

An electrode connector 32, speaker 34, and diagnostic display panel 36 are disposed on case 12 within electrode compartment 26. Diagnostic display panel 36 is disposed adjacent to illuminatable resume/rescue switch 18. Diagnostic display panel 36, which is appropriately a membrane switch panel, includes visual "Battery Status" indicator light 38, "Electrodes" indicator light 40, "Service" indicator light 42, and a sensor area 47. An instruction and safety label is located in the inside surface of lid 28. Electrodes 50 are removably connected to electrode connector 32. Electrodes 50 typically include a pair of electrodes for attachment to patient in a sealed package.

When lid 28 is closed, magnet 29 is positioned directly over sensor area 47. Lid open detection circuit 8 is located beneath sensor area 47. Lid open detection circuit 8 is preferably a solid state Hall effect switch circuit 51 incorporating a Hall effect sensor 52. In the preferred embodiment of the invention, the Hall effect sensor 52 is a model SS441A manufactured by Honeywell Inc. of Minneapolis, Minn., however, other Hall effect sensors 52 may be used without departing from the spirit or scope of the present invention.

Figure 3:
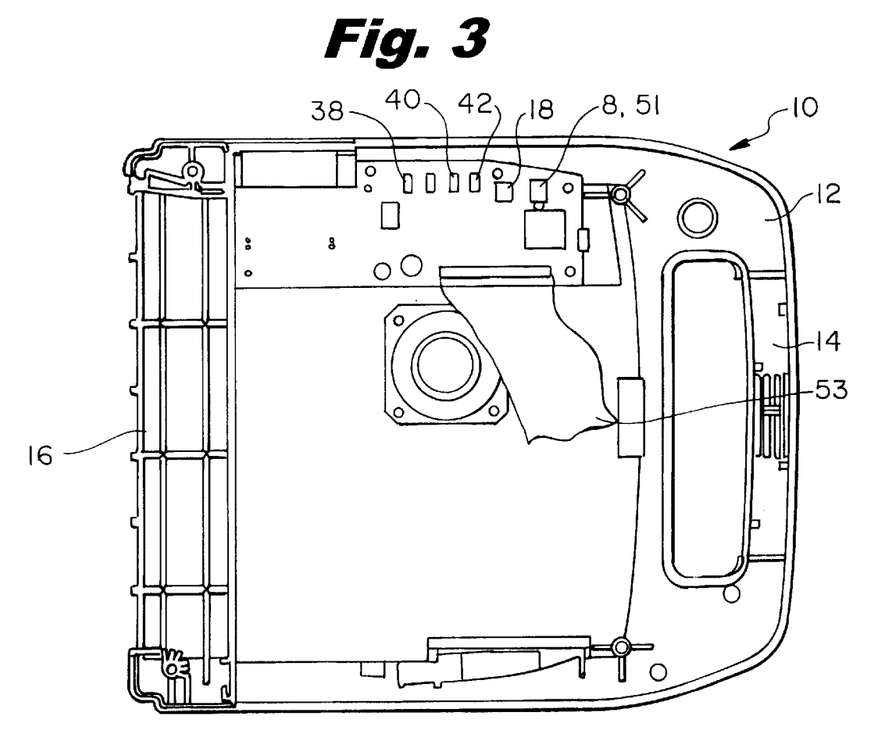
FIG. 3 is a cut away of the AED illustrating a wiring harness and a diagnostic panel.

FIG. 3 is a cut away view of AED 10 illustrating the backside of diagnostic panel 36 and the mounted position of lid open detection circuit 8 on that backside. As shown, a single flex circuit wiring harness 53 is provided to connect diagnostic panel 36 and its components including lid open detection circuit 8 to the main circuitry (or electrical system) of AED 10.

Figure 4:
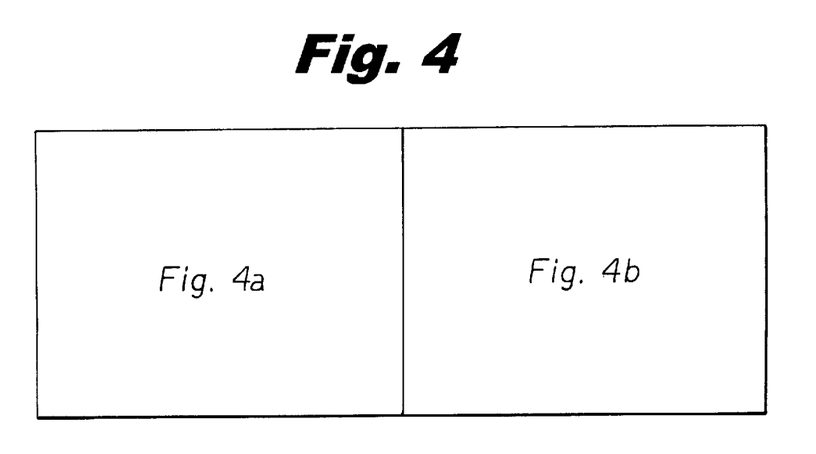
FIG. 4 is a schematic diagram of a lid open detection circuit according to the present invention.
Figure 4A:
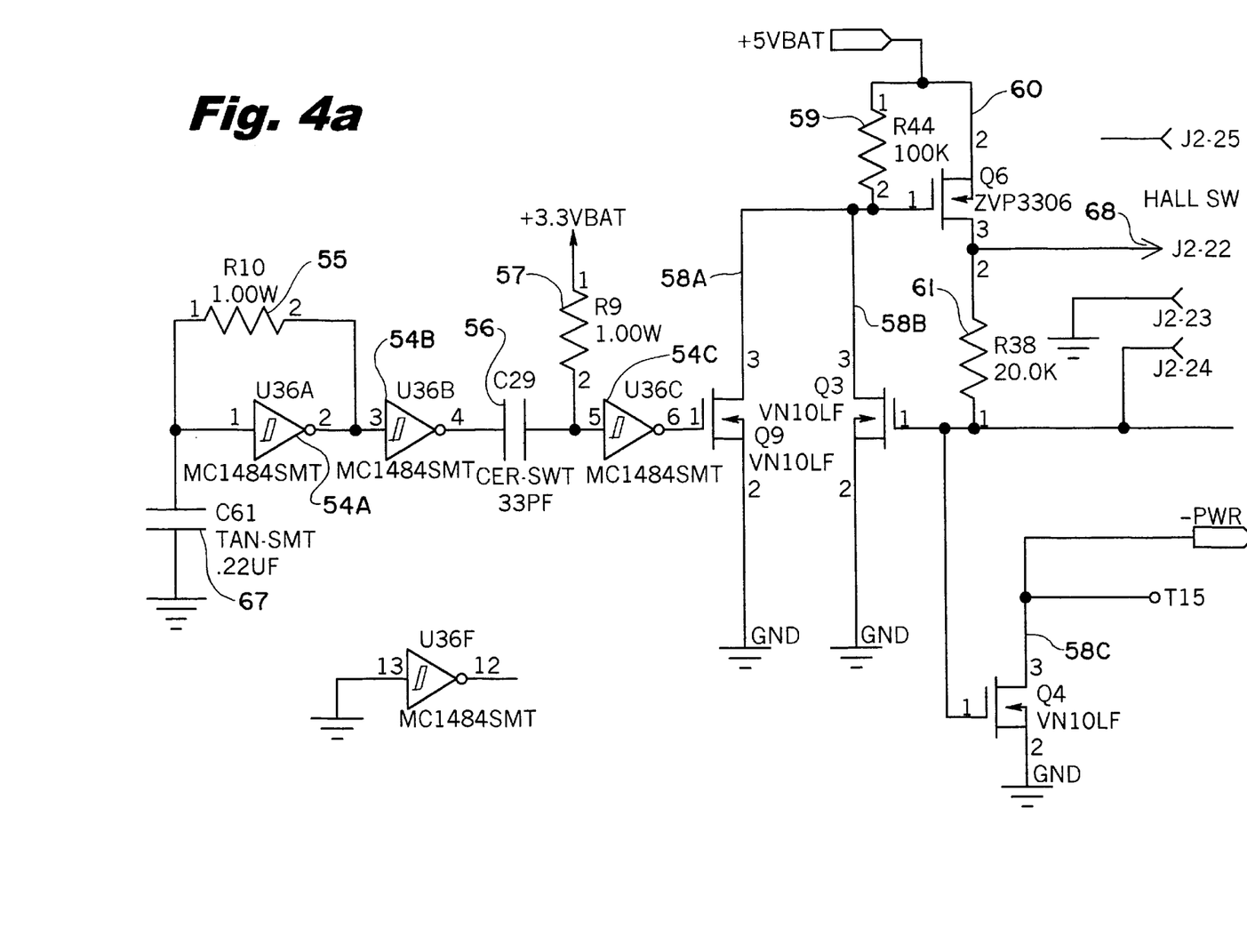
Figure 4B:
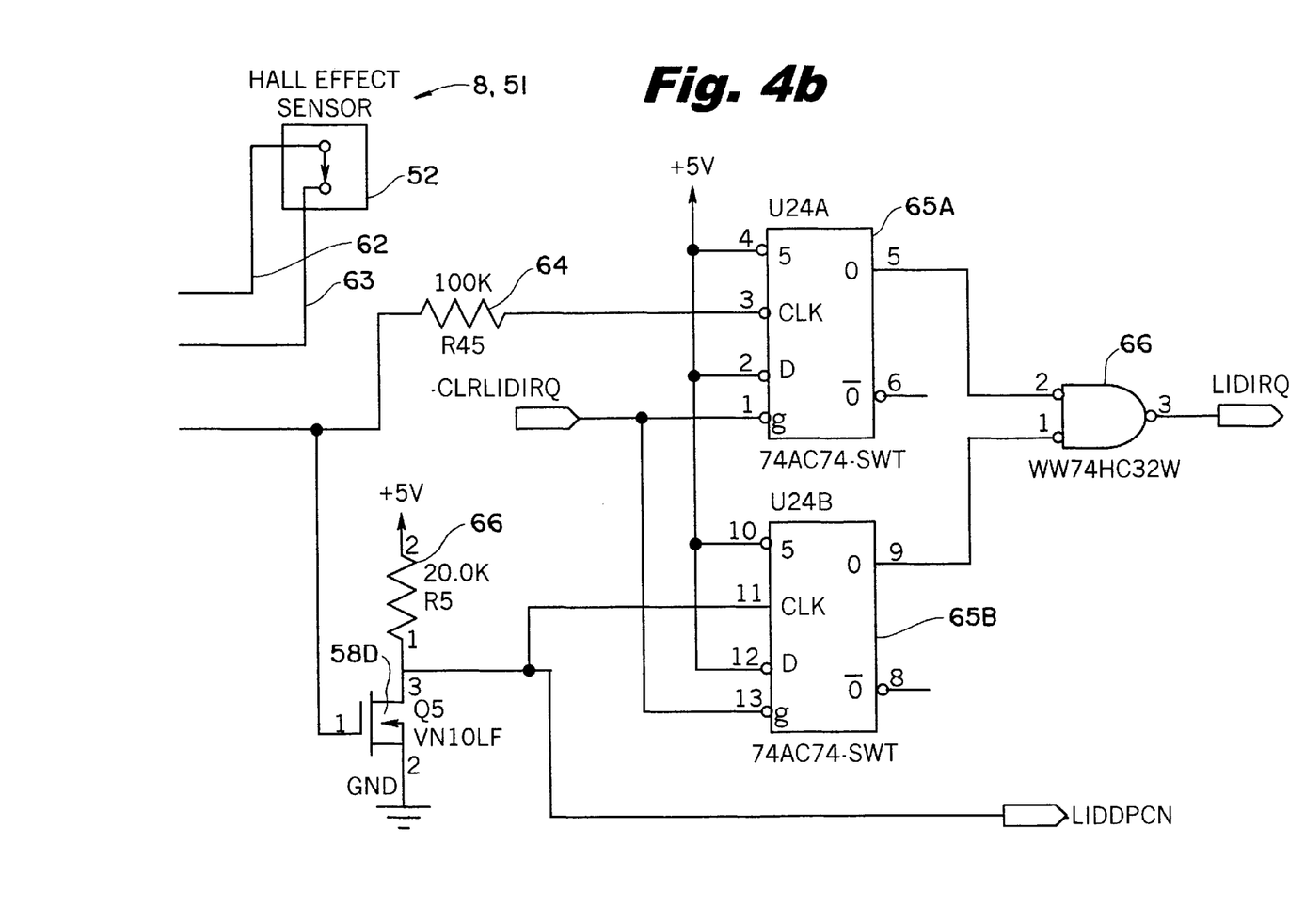

FIG. 4 is a schematic diagram of lid open detection circuit 8 of the present invention namely, Hall effect switch circuit 51. The Hall effect switch circuit 51 changes between two states that alternate depending on the location of the state changing means, magnet 29. The first state acts to power ON AED 10 and occurs when magnet 29 and the magnetic field created by magnet 29 are moved away from sensor area 47 and the underlying Hall effect sensor 52. The second state acts to power OFF AED 10 and occurs when magnet 29 and its magnetic field are moved proximate sensor area 47 and the underlying Hall effect sensor 52.

Hall effect switch circuit 51 begins with an inverter gate 54A connected in parallel with resistor 55 which lies between the anode of capacitor 67 and inverter gate 54B. The output of inverter gate 54B is tied to capacitor 56. Capacitor 56 is connected to a resistor 57, which is connected to a 3.3V power supply, and to the input of inverter gate 54C. The output of inverter gate 54C is coupled to the gate of MOSFET 58A. The drain of MOSFET 58A is connected to the drain of MOSFET 58B which is connected to resistor 59 and gate of MOSFET 60. Resistor 59 is tied to a 5V power supply and to the source of MOSFET 60. The drain of MOSFET 60 is connected to resistor 61 which is connected to the gate of MOSFET 58B. Also connected to the gate of MOSFET 58B is the gate of MOSFET 58C. Hall effect sensor 52 has a first contact 62 tied to ground and a second contact 63 connected to the gate of MOSFET 58B. A resistor 64 is connected to the gate of MOSFET 58B to D-type flip-flop 65A. The gate of MOSFET 58B is also connected to the gate of MOSFET 58D whose drain is connected to a resistor 66 that is connected to a 5V power supply. The drain of MOSFET 58D is also connected to a D-type flip-flop 65B. The outputs of each of the D-type flip-flops 65A and 65B are connected to an AND gate 66. Hall effect sensor 52 receives power at node designated 68.

In operation, Hall effect switch circuit 51 functions as described below. Inverter gate 54A and inverter gate 54B form an oscillator and buffer that has a cycle time of approximately 200 milliseconds. The pulse from inverter gate 54B is differentiated by capacitor 56 and resistor 57 to form a positive and then a negative pulse of about 30–50 microsecond duration. Since resistor 57 is pulling the input to inverter gate 54C high, the positive pulse does nothing, but the negative pulse forces the input to inverter gate 54C low for approximately 30–50 microseconds causing the output of inverter gate 54C to go high for 30–50 microseconds. This in turn causes MOSFET 58A to turn on and its drain to go low for 30–50 microseconds. MOSFET 60, which is a p-channel device, turns on when its gate is pulled low and causes its drain to be pulled high. This action applies a positive voltage and thereby, power to node 68 and pullup to node 63 which allows the Hall effect sensor 52 to monitor the magnetic field near it. If the Hall effect sensor 52 has a magnetic field near it, it will act like a closed switch between contact 62 and contact 63. A closed switch action clamps the gate of MOSFET 58B to a low value and does not allow it to turn on. When the pulse ends and MOSFET 58A turns off, Hall effect switch circuit 51 just shuts off and waits for the next clock pulse.

If, however, the magnetic field is not present, as when the lid 28 is opened, the Hall Effect sensor 52 does not turn on and resistor 61 is allowed to pull the gate of MOSFETs 58B and 58C high.Hall effect switch circuit 51 will remain in this energized state until a magnetic field is applied once again to the Hall effect sensor 52.

MOSFET 58C is turned on as well when lid 28 is opened and energizes the main power circuits of AED 10. MOSFET 58D generates a steady 'LIDOPEN' signal used by microprocessor 74 to determine what caused it to power up. Resistor 61 also pulls the clock pin high on D-type flip-flop 65A which causes a lid interrupt to be sent to the microprocessor 74. When lid 28 is closed the 'LIDOPEN' signal rises and causes D-type flip-flop 65B to be set which creates an interrupt again to let the microprocessor 74 know that lid 28 has been shut. The interrupt latches of D-type flip-flops 65A and 65B are reset by the microprocessor 74 through the signal 'CLRLIDIRQ.'

Hall effect switch circuit 51 is designed to check the status of lid 28 to determine whether it is open or closed, and to alert microprocessor 74 in either event to control the main power to AED 10. The Hall effect sensor 52 is a "snap action" type device which has built-in hysteresis and an output that is either on or off, i.e. high logic level or low logic level. Hall effect sensor 52 uses a relatively high amount of current to operate. In view of the limited supply of power available from battery 80, Hall effect switch circuit 51 is able to reduce the average current to increase the battery life. This is accomplished by turning on Hall effect sensor 52 for only 30–50 microseconds every 200 milliseconds. Such a timing sequence enables the Hall effect sensor 52 to detect a lid open status quickly enough so that an operator will not notice a delay and yet operates for a short enough time so as not to drain battery 80.

It should be noted that other switching means besides Hall effect switch circuit 51 may be used as the lid open detection circuit 8. For instance, a device such as a microswitch, an optical switch or a relay switch might be used without departing from the spirit or scope of the invention.

Figure 5:
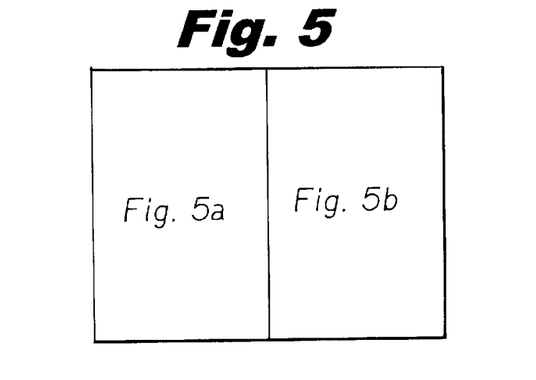
FIG. 5 is a block diagram of the electrical system of the AED shown in FIG.'S 1–3.
Figure 5A:
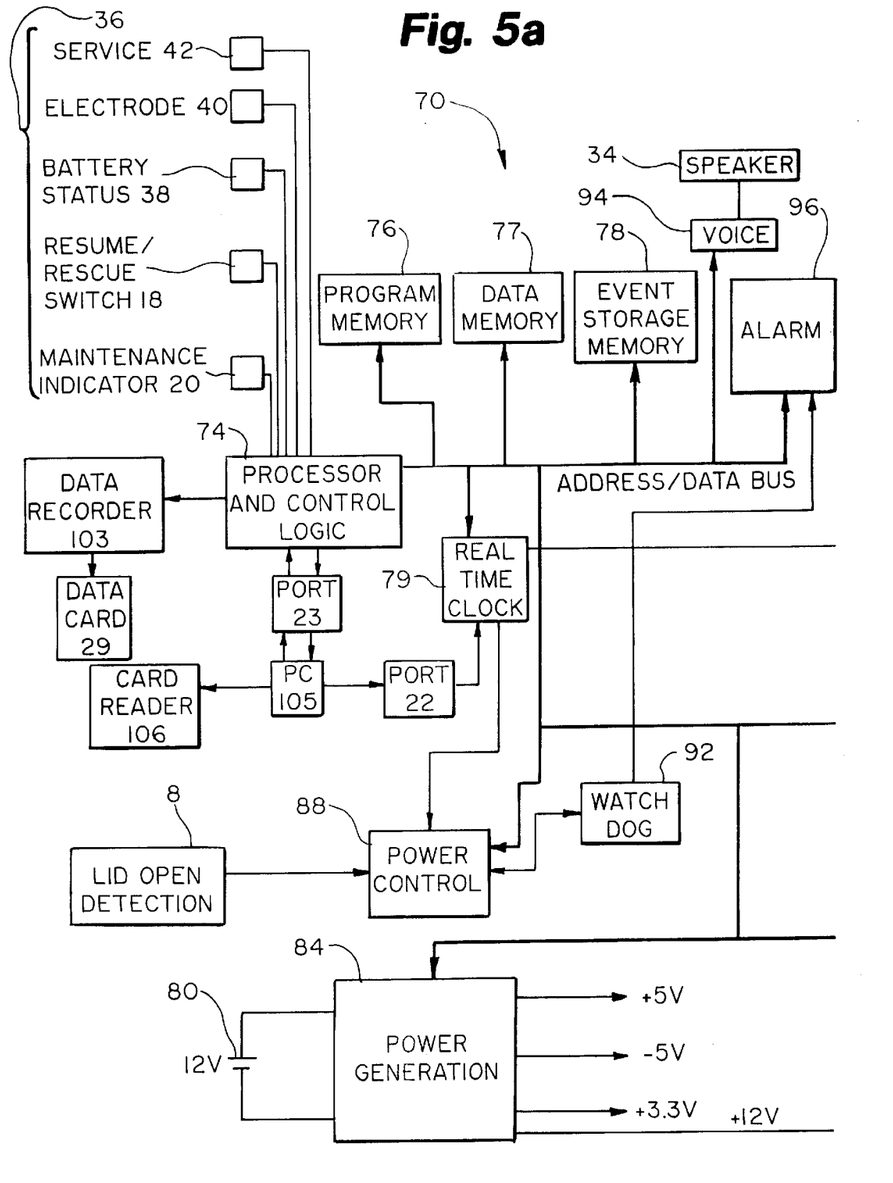
Figure 5B:
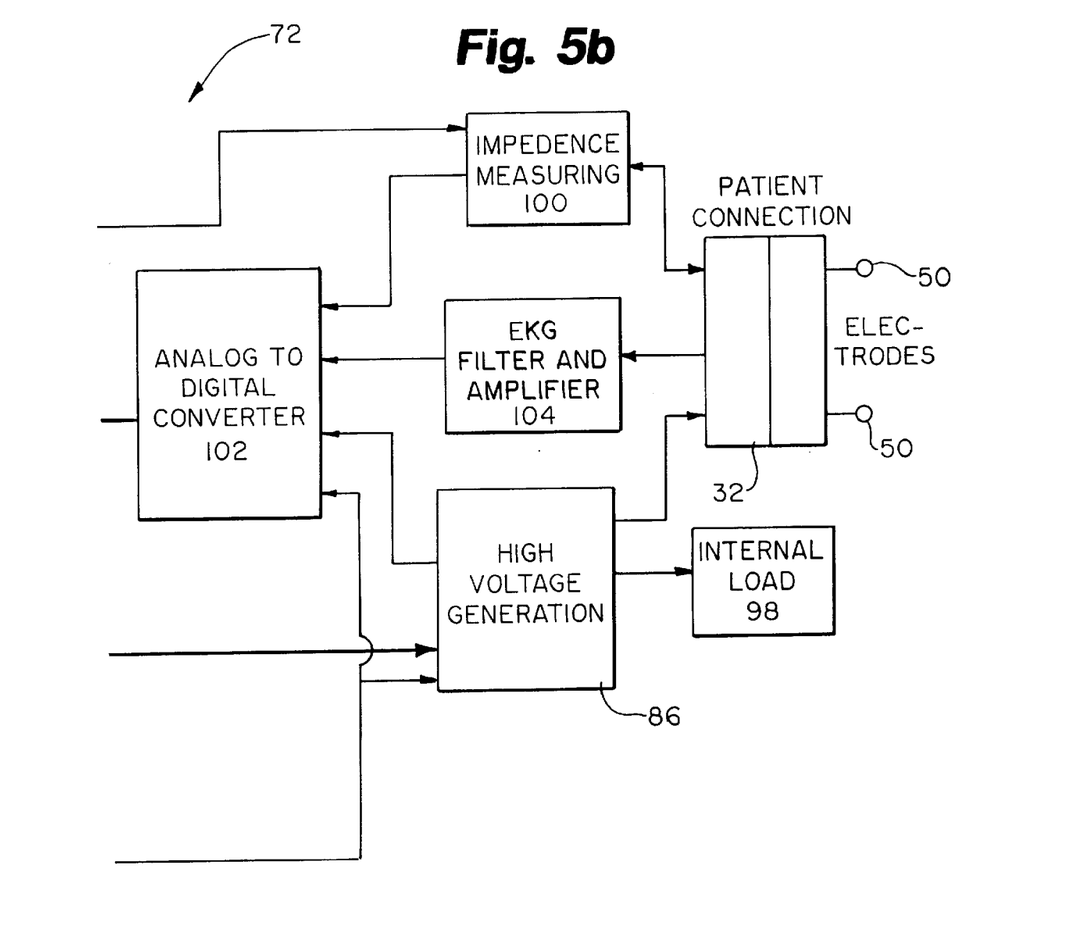

FIG. 5 is a block diagram of the electrical system 70 of AED 10 and depicts the lid open detection circuit 8 relative the other components of system 70. In general, the overall operation of AED 10 is controlled by a digital microprocessor-based control system 72 which includes a processor 74 interfaced to program memory 76, data memory 77, event memory 78 and real time clock 79. The operating program executed by processor 74 is stored in program memory 76. Data memory 77 is used by processor 74 as a scratch pad memory during the execution of the operating program.

Electrical power is preferably provided by a lithium sulphur dioxide battery 80 which is enclosed in battery pack 16, battery pack 16 being removably positioned within the battery compartment. Battery 80 may be comprised of a plurality of battery cells that are electrically coupled together. Battery 80 is connected to power generation circuit 84. "Battery Status" indicator light 38 indicates the charge status of battery 80 and prompts the operator to replace battery 80 when needed.

During normal operation, power generation circuit 84 generates a 12V supply and regulated 3.3V and ±5V supplies with the power provided by battery 80. The +5V output of battery 80 functions as a back-up battery to power components of electrical system 70 during the execution of self-tests and to activate maintenance indicators and alarms (as described below). The 3.3V supply is generally used to power real time clock 79, lid open detection circuit 8 and watch dog timer 92 when lid 28 is closed, or in other words, when AED 10 is in a stand-by mode. Although not separately shown in FIG. 5, power generation circuit 84 includes voltage level sensing circuits which are coupled to processor 74. The voltage level sensing circuits provide low battery level signals to processor 74.

Power generation circuit 84 is also connected to power control circuit 88 and processor 74. Power control circuit 88 is also connected to lid open detection circuit 8, watch dog timer 92, real time clock 79 and processor 74. Serial connector port 23 is coupled to processor 74 for two-way serial data transfer using an RS-232 protocol. Resume/rescue switch 18 and the "rescue" and "resume" indications thereof, maintenance indicator 20, and "Battery Status" indicator light 38, "Electrodes" indicator light 40, and "Service" indicator light 42 of diagnostic display panel 36, voice circuit 94 and piezo electric audible alarm 96 are also connected to processor 74. Voice circuit 94 is connected speaker 34. In response to voice prompt control signals from processor 74, circuit 94 and speaker 34 generate audible voice prompts.

High voltage generation circuit 86 is also connected to and controlled by processor 74. High voltage generation circuits, such as circuit 86, are generally known and disclosed, for example, in the commonly assigned Persson et al. U.S. Pat. No. 5,405,361, which is hereby incorporated by reference. In response to charge control signals provided by processor 74, high voltage generation circuit 86 is operated in a charge mode during which one set of semiconductor switches (not separately shown) cause a plurality of capacitors (also not shown) to be charged in parallel to about 200V to 1000V each, by power supplied by power generation circuit 84. Once charged, and in response to discharge control signals provided by processor 74, high voltage generation circuit 86 is operated in a discharge mode during which the capacitors are discharged in series by another set of semiconductor switches (not separately shown) to produce the high voltage defibrillation pulses. The defibrillation pulses are applied to the patient through electrode connector 32 which is connected to high voltage generation circuit 86. Under certain circumstances described below, processor 74 causes high voltage generation circuit 86 to be discharged through an internal resistive load 98 rather than connector 32.

Impedance measuring circuit 100 is connected to electrode connector 32 and real time clock 79, and is interfaced to processor 74 through analog-to-digital (A/D) converter 102. The impedance measuring circuit 100 receives a clock signal having a predetermined magnitude from clock 79, and applies the signal to electrodes 50 through connector 32. The magnitude of the clock signal received back from electrodes 50 through connector 32 is monitored by impedance measuring circuit 100. An impedance signal representative of the impedance present across connector 32 is then generated by circuit 100 as a function of the ratio of the magnitudes of the applied and received clock signals (i.e., the attenuation of the applied signal). If the conductive adhesive on electrodes 50 is dried out, if electrodes 50 are not properly connected to connector 32, or if electrodes 50 are not properly positioned on the patient, a relatively high resistance (e.g., greater than about two hundred ohms) will be present across connector 32. The resistance across connector 32 will be between about twenty-five and one hundred eighty ohms when fresh electrodes are properly positioned on the patient with good electrical contacts. The impedance signal representative of the impedance measured by circuit 100 is digitized by A/D converter 102 and provided to processor 74.

AED 10 also includes a data recorder 102 that is interfaced to processor 74 and positioned internally within AED 10 adjacent to data card slot 24. AED 10 further includes an electrocardiogram (ECG) filter and amplifier 104 which is connected between electrode connector 32 and A/D converter 102. The ECG or cardiac rhythm of the patient is processed by filter and amplifier 104 in a conventional manner, and digitized by A/D converter 102 before being coupled to processor 74.

The rescue mode of operation of AED 10 is initiated when an operator opens lid 28 to access electrodes 50. The opening of lid 28 is detected by lid open detection circuit 8, which powers ON AED 10. In response to this action, power control circuit 88 activates power generation circuit 84 and initiates the rescue mode operation of processor 74. Processor 74 than begins its rescue mode operation by switching maintenance indicator 20 to a maintenance required state (e.g., a red visual display in one embodiment), flashing the "rescue" light associated with resume/rescue switch 18 and the indicator lights on diagnostic display panel 36, and performing a lid opened self-test.

During the lid opened self-test, processor 74 checks at least the following: 1) the charge state of battery 80; 2) the interconnection and operability of electrodes 50; 3) the state of event memory 78; 4) the functionality of real time clock 79; and 5) the functionality of A/D converter 102. The charge state of battery 80 is checked by monitoring the voltage level signals provided by power generation circuit 84. If battery 80 is determined to have a low charge, the "battery status" indicator 38 on diagnostic display panel 36 will indicate the sensed status. The interconnection and operability of electrodes 50 are checked by monitoring the impedance signals provided by impedance measuring circuit 100. If electrodes 50 are missing or unplugged from connector 32, or if electrodes 50 are damaged, processor 74 will illuminate "Electrodes" indicator light 40 in diagnostic display panel 36.

Further, during the lid opened self-test, processor 74 accesses the event memory 78 to determine whether data from a previous rescue operation are still stored in memory. If so, processor 74 causes the "resume" indicator associated with resume/rescue switch 18 on diagnostic panel 36 to be illuminated, and initiates the generation of a "clear memory" voice prompt. If resume/rescue switch 18 is pressed by the operator following the activation of these indicators, processor 74 clears event memory 78 and proceeds with its rescue mode of operation. The functionality of real time clock 79 and A/D converter 102 are checked by monitoring the outputs of these circuit elements for expected signals. Diagnostic display panel "service" light 42 is illuminated by processor 74 if faults are identified in either of real time clock 79 or A/D converter 102.

If the lid opened self-test is successfully completed, processor 74 switches maintenance indicator 20 to an operational state and initiates the rescue mode of operation of AED 10. The rescue mode of operation generates audible voice prompts through speaker 34 to guide the user through the operations of AED 10 and if necessary, delivery of a defibrillation pulse. AED 10 determines its rescue mode steps of operation by monitoring the impedance across electrode connector 32 and by monitoring the patient's cardiac rhythm.

The closing of lid 28 is detected by lid open detection circuit 8 and initiates the powering OFF of AED 10. During the powering OFF of AED 10, processor 74 initiates and performs a lid closed self-test. During the lid closed self-test processor 74 performs a comprehensive check of the status and functionality of AED 10, including: 1) the state of event memory 78; 2) the functionality of real time clock 79; 3) the functionality of A/D convertor 102; 4) the functionality of program memory 76, data memory 77 and event memory 78; 5) the charge state of battery 80; and 6) the interconnection and operability of electrodes 50. The state of event memory 78, the state of battery 80, the interconnection and operability of electrodes 50, and the functionality of real time clock 79 and A/D converter 102 are checked in a manner identical to that described above with reference to the lid opened self-test.

Conventional memory test routines are implemented to check the functionality of program memory 76, data memory 77, and event memory 78. Maintenance indicator 20 is switched to its maintenance required state by processor 74 if faults are identified in the charge state of battery 80 or the interconnection or functionality of electrodes 50 during the lid closed self-test.

A daily self-test is initiated and performed by processor 74 at a predetermined time each day (e.g. every twenty-four hours). During the daily self-test, processor 74 performs all the component check operations described above that are performed during the lid opened and lid closed self-tests. In addition to illuminating the appropriate lights on diagnostic display panel 36, processor 74 leaves maintenance indicator 20 in its maintenance required state if faults are identified during the daily self-test.

Processor 74 also initiates and performs a weekly self-test at a predetermined time one day each week. During the weekly self-test processor 74 performs all the component check operations described above that are performed during the daily-self-test. In addition, processor 74 causes high voltage generation circuit 86 to sequentially operate in its charge and discharge modes, with the charge being dumped to an internal resistive load 98. While the high voltage generation circuit 86 is operating in the charge mode, processor 74 monitors the time required to charge the circuit's capacitors and the capacitor voltage. A fault is identified if either is out of nominal conditions. Maintenance indicator 20 and alarm 96 are actuated n the manner described above if any faults are identified during the weekly self-test. Note that all performed test and patient data may be recorded in event memory 78.

Watch dog timer 92 is set to time watch dog time-out periods of about thirty hours (e.g., a period greater than twenty-four hour periods between daily self-tests), and is reset by processor 74 at the beginning of each daily self-test and each time lid 28 is opened. In the event control system 70 malfunctions and watch dog timer 92 times out, internal hardware switches maintenance indicator 20 to the maintenance required state and processor 74 actuates alarm 96 to alert an operator to the fact that AED 10 requires maintenance.

The present invention may be embodied in other specific forms without departing from the spirit of the essential attributes thereof; therefore, the illustrated embodiment should be considered in all respects as illustrative and not restrictive, reference being made to the appended claims rather than to the foregoing description to indicate the scope of the invention.

What is claimed:

1. An automated external defibrillator (AED) comprising:
    a housing;
    an openable lid formed in said housing; and
    a lid open detection circuit contained within said housing wherein the AED is powered ON when said lid open detection circuitry detects said openable lid has been opened and, wherein the AED is powered OFF when said lid open detection circuit detects said openable lid has been closed, said lid open detection circuit being mounted on a membrane panel.

2. The defibrillator of claim 1, wherein a plurality of indicators are mounted on said membrane panel proximate said lid open detection circuit and wherein said membrane panel has a single wiring harness.

3. An automated external defibrillator (AED) comprising:
    a housing;
    an openable lid formed in said housing having a state changing device mounted thereon; and
    a lid open detection circuit having a switch contained within said housing, said switch having a first state for powering ON said AED when said openable lid is open and having a second state for powering OFF said AED when said openable lid is closed, said lid open detection circuit being mounted on a membrane panel having a single wiring harness.

4. The defibrillator of claim 3, wherein a plurality of indicators are mounted on said membrane panel proximate said lid open detection circuit and wherein said membrane panel has a single wiring harness.

5. A lid open detection circuit for powering ON an automated external defibrillator (AED) wherein said AED has a housing and an openable lid formed in said housing, comprising:
    a Hall effect switch contained within said housing, said Hall effect switch adapted to power ON said AED when said openable lid is open and adapted to power OFF said AED when said openable lid is closed, said Hall effect switch being located below a sensor area.

6. The circuit of claim 5, wherein said sensor area is located on a membrane panel.

* * * * *